March 9, 1948. J. H. VAN BARNEVELD Plant Pat. 788

ROSE PLANT

Filed Feb. 28, 1947

Inventor
J. H. Van Barneveld
by Robert Tobk
attorney

Patented Mar. 9, 1948

Plant Pat. 788

UNITED STATES PATENT OFFICE

788

ROSE PLANT

John H. van Barneveld, Puente, Calif., assignor to The Conard-Pyle Company, West Grove, Pa., a corporation of Pennsylvania Application February 28, 1947, Serial No. 731,441

1 Claim. (Cl. 47—61)

The present discovery relates to a new and distinct variety of rose plant, originating as a sport of the rose "Mme. Henri Guillot" (Pl. Pat. No. 337), and distinguishing therefrom dominantly by its climbing habit.

The parent plant is a bush rose of the hybrid tea class and is notable for its extraordinary vigor, its leathery and deep green foliage, the urn shape and distinctive coloring of its bud and flower.

Of primary importance here, however, is the fact that this parent variety has never, so far as I am aware, exhibited a climbing habit, its growth being that of the average strong bush rose.

This new sport is half hardy, tall and particularly useful for cut flowers and garden decoration.

Figure 1:
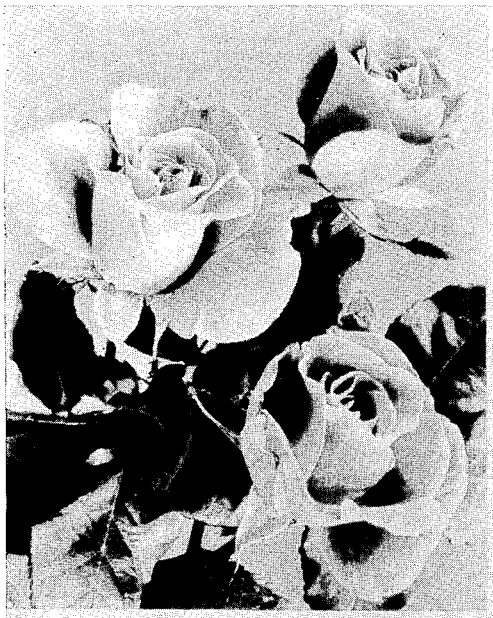
Figure 2:
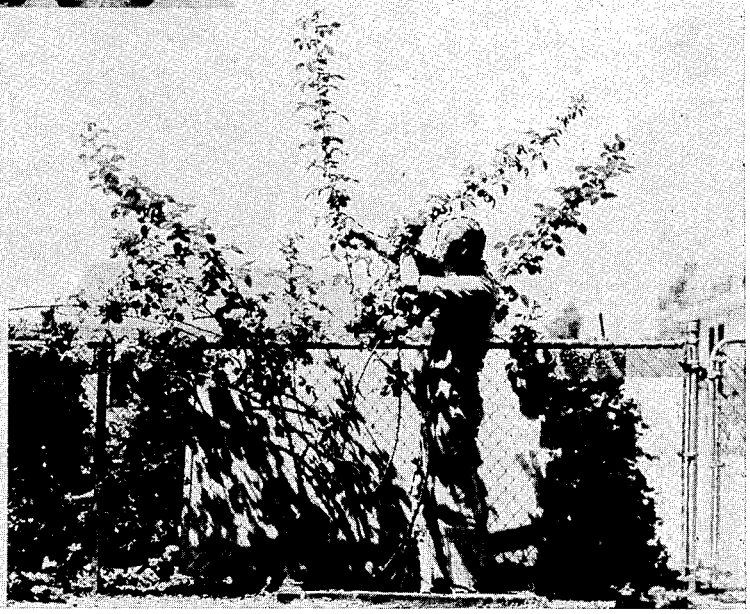

In the drawing, Figure 1 shows specimens of the blooms of this new variety, and Figure 2 illustrates a specimen plant in comparison with the height of an average person as represented in broken lines to thereby depict the unusual height to which it grows—several times that of the parent variety—with great vigor and strength.

Aside from this climbing habit, the new variety has the same general characteristics that are present in its parent bush variety, having reference to its foliage, color of bud and flowers, etc. It is, therefore, unnecessary to describe the plant in detail since it conforms to the description contained in the above-named patent for the parent variety, excepting only as to the parent's habit of growth as a bush.

The new variety has been asexually reproduced by budding, and the climbing characteristic noted appeared to be fully established and transmitted to the progeny.

I claim:

A new and distinct variety of rose plant, having a similarity to its parent in respect to its leathery and deep green foliage, and urn shape and distinctive coloring of its bud and flower, but distinguished therefrom by its strong and vigorous climbing habit, substantially as shown and described.

JOHN H. VAN BARNEVELD.